United States Patent
Arca et al.

(10) Patent No.: US 7,880,045 B2
(45) Date of Patent: *Feb. 1, 2011

(54) PROCESS FOR THE CATALYTIC HYDRODEALKYLATION OF ALKYLAROMATIC HYDROCARBONS

(75) Inventors: Vittorio Arca, Chioggia-Venezia (IT); Angelo Boscolo Boscoletto, Sottomarina-Venezia (IT)

(73) Assignee: Polimeri Europa S.p.A., Brindisi (IT)

( * ) Notice: Subject to any disclaimer, the term of this patent is extended or adjusted under 35 U.S.C. 154(b) by 903 days.

This patent is subject to a terminal disclaimer.

(21) Appl. No.: 10/586,586

(22) PCT Filed: Dec. 13, 2004

(86) PCT No.: PCT/EP2004/014165
§ 371 (c)(1),
(2), (4) Date: Dec. 7, 2006

(87) PCT Pub. No.: WO2005/071045
PCT Pub. Date: Aug. 4, 2005

(65) Prior Publication Data
US 2007/0203377 A1    Aug. 30, 2007

(30) Foreign Application Priority Data
Jan. 22, 2004    (IT) .................. MI2004 A000077

(51) Int. Cl.
*C07C 6/12* (2006.01)
(52) U.S. Cl. ..................................... 585/488; 585/489
(58) Field of Classification Search ................. 585/488, 585/489
See application file for complete search history.

(56) References Cited

U.S. PATENT DOCUMENTS

| | | | |
|---|---|---|---|
| 4,351,979 A | 9/1982 | Chester et al. | |
| 5,689,027 A | 11/1997 | Abichandani et al. | |
| 5,877,374 A | 3/1999 | Nacamuli et al. | |
| 6,063,975 A | * 5/2000 | Drake et al. | ................. 585/418 |

FOREIGN PATENT DOCUMENTS

| | | |
|---|---|---|
| EP | 0 109 962 | 6/1984 |
| EP | 138 617 | 4/1985 |

OTHER PUBLICATIONS

U.S. Appl. No. 12/375,830, filed Jan. 30, 2009, Arca, et al.
U.S. Appl. No. 10/594,076, filed Sep. 22, 2006, Arca, et al.

* cited by examiner

*Primary Examiner*—Thuan Dinh Dang
(74) *Attorney, Agent, or Firm*—Oblon, Spivak, McClelland, Maier & Neustadt, L.L.P.

(57) ABSTRACT

Process for the catalytic hydrodealkylation alone of hydrocarbons, comprising $C_8$-$C_{13}$ alkylaromatic compounds, optionally mixed with $C_4$-$C_9$ aliphatic and cycloaliphatic products, which comprises treating said hydrocarbon compositions, in continuous and in the presence of hydrogen, with a catalyst consisting of a ZSM-5 zeolite, as such or in a bound form, wherein the Si/Al molar ratio in the ZSM-5 ranges from 5 to 35, modified with at least one metal selected from those belonging to groups IIB, VIB, VIII, at a temperature ranging from 400 to 650° C., a pressure ranging from 2 to 4 MPa and a $H_2$/charge molar ratio ranging from 3 to 6.

17 Claims, No Drawings

PROCESS FOR THE CATALYTIC HYDRODEALKYLATION OF ALKYLAROMATIC HYDROCARBONS

The present invention relates to a process for the catalytic hydrodealkylation of alkylaromatic hydrocarbons.

More specifically, the present invention relates to a process for the catalytic hydrodealkylation of hydrocarbon compositions comprising $C_8$-$C_{13}$ alkylaromatic compounds, optionally mixed with $C_4$-$C_9$ aliphatic and cycloaliphatic products.

Even more specifically, the present invention relates to a process for the catalytic hydrodealkylation of alkylaromatic hydrocarbons, mixed with aliphatic products, in which concomitant transalkylation, isomerization, disproportioning and condensation reactions are almost quantitatively suppressed. This leads to a high production of benzene, toluene and ethane (BTE), and the reduced or non-formation of methane and condensed products, essentially naphthalene and biphenyl products.

Processes for the catalytic hydrodealkylation of alkylaromatic hydrocarbons are known in literature. European patent 138,617 describes, for example, a process for converting alkylaromatic hydrocarbons by means of hydrodealkylation which comprises treating a hydrocarbon stream, essentially consisting of ethylbenzene and xylenes, under conventional reaction conditions with a zeolitic catalyst modified with molybdenum. In the process described, however, the general reaction conditions do not allow a hydrodealkylation reaction without there being contemporaneous isomerization, transalkylation, disproportioning and condensation reactions. The limitations towards a selective catalytic hydrodealkylation also emerge from various other processes described in the known art. In some of these, said reaction actually forms a secondary reaction with respect to the isomerization, transalkylation, disproportioning and condensation reactions.

The Applicant has now found that it is possible to effect the catalytic hydrodealkylation alone of $C_8$-$C_{13}$ alkylaromatic hydrocarbons to benzene, toluene and ethane (BTE) without the concomitant transalkylation, disproportioning, isomerization and condensation reactions which always characterize the processes of the known art, by selecting suitable operating conditions and formulation of a zeolitic catalyst.

In particular, under the operating conditions and with the composition of the catalyst of the present invention, it has been surprisingly found that the hydrodealkylation reaction is not only quantitatively selective towards the formation of benzene and toluene, but that the benzene/toluene ratio is always distinctly favourable with respect to benzene. The economical advantage of the process can therefore be related to the intrinsic value of both reaction streams: the liquid phase for the remunerative benzene and toluene value, with particular regard to the benzene always produced in higher quantities than toluene; the gaseous phase for the possibility of recycling the ethane produced in any pyrolytic process, for example for recycling to the ovens, with a considerable recovery of energy which this recycling guarantees.

An object of the present invention therefore relates to a process for the catalytic hydrodealkylation process alone of hydrocarbon compositions comprising $C_8$-$C_{13}$ alkylaromatic compounds, optionally mixed with $C_4$-$C_9$ aliphatic and cycloaliphatic products, which comprises treating said hydrocarbon compositions, in continuous and in the presence of hydrogen, with a catalyst consisting of a ZSM-5 zeolite carrier medium, having an Si/Al molar ratio ranging from 5 to 35, modified with at least one metal selected from those belonging to groups IIB, VIB, VIII, at a temperature ranging from 400 to 650° C., preferably from 450 to 580° C., a pressure ranging from 2 to 4 MPa, preferably from 2.8 to 3.6 MPa, and a $H_2$/charge molar ratio ranging from 3 to 6, preferably from 3.8 to 5.2.

According to the present invention, the hydrocarbon charge subjected to hydrodealkylation comprises $C_8$-$C_{13}$ alkylaromatic compounds, such as ethylbenzene, xylenes, diethylbenzenes, ethylxylenes, trimethylbenzenes, tetramethybenzenes, propylbenzenes, ethyltoluenes, propyltoluenes, etc. Said charge can derive, for example, from the effluents of reforming units or from units forming pyrolytic processes, such as steam cracking, and optionally contain a mixture of $C_4$-$C_9$ aliphatic and cycloaliphatic products, and organic compounds containing hetero-atoms, such as, for example, sulfur, in the typical quantities generally present in charges coming from reforming units or pyrolytic processes.

The hydrocarbon charge used in the present process can also be subjected to separation treatment, for example distillation or extraction, to concentrate the products to be subjected to subsequent hydrodealkylation, or it can be treated with aromatization processes to increase the concentration of alkylaromatics and reduce the concentration of paraffins. A previous hydrogenation of the charge may also be necessary to eliminate the unsaturations present in the aliphatic compounds and on the same alkyl substituents of the aromatic rings. The same hydrogenation can remove sulfur, nitrogen or oxygen from the substances typically present in the charge to be treated, even if this latter aspect is not particularly important as, under the catalytic hydrodealkylation conditions, according to the present invention, these hetero-atoms are quantitatively removed (for example, sulfur as $H_2S$).

The hydrodealkylation catalyst, according to the present invention, consists of a ZSM-5 zeolite modified with at least one metal selected from those of groups IIB, VIB and VIII, in particular molybdenum, zinc, nickel, cobalt, palladium, or their mixtures consisting for example of molybdenum/zinc and molybdenum/cobalt, wherein the metals exert a cooperative effect on the hydrodealkylation. Among the metals object of the invention, taken either singly or in pairs, molybdenum is the preferred metal. The composition of the zeolitic carrier medium is particularly important for the embodiment of the present invention which envisages the hydrodealkylation of alkylaromatic compounds in the substantial absence of secondary isomerization, transalkylation, disproportioning and condensation reactions. It has in fact been verified that the use of a ZSM-5 zeolite rich in aluminum, in particular with Si/Al molar ratios ranging from 5 to 35, preferably from 15 to 30, has contributed to obtaining the desired result.

ZSM-5 zeolite is available on the market or can be prepared according to the methods described in U.S. Pat. Nos. 3,702,886 and 4,139,600. The structure of the ZSM-5 zeolite is described by Kokotailo et al. (Nature, Vol. 272, page 437, 1978) and by Koningsveld et al. (Acta Cryst. Vol. B43, page 127, 1987; Zeolites, Vol. 10, page 235, 1990).

In the process, object of the present invention, it is preferable to use the zeolitic catalyst in a bound form, using a binding substance which gives it shape and consistency, for example mechanical resistance, so that the zeolite/binder catalyst is suitable for being conveniently used in an industrial reactor. Examples of binders include aluminas, among which pseudo-bohemite and γ-alumina; clays, among which kaolinite, vermiculite, attapulgite, smectites, montmorillonites; silica; alumino-silicates; titanium and zirconium oxides; combinations of two or more of these, using in such quantities as to give zeolite/binder weight ratios ranging from 100/1 to 1/10.

The dispersion of the metals in the zeolite or zeolite/binder catalyst can be carried out according to the conventional techniques, such as impregnation, ion exchange, vapour deposition, or surface adsorption. The incipient impregnation technique is preferably used, with an aqueous or aqueous-organic solution (with the organic solvent preferably selected from alcohols, ketones and nitriles or their mixtures), containing at least one hydro- and/or organo-soluble compound of the metal, with a total final content of the metal in the catalyst ranging from 0.5 to 10% by weight.

The zeolite, with or without binder, is subjected to impregnation with a metal of groups IIB, VIB and VIII. In particular, the catalyst, whether it be bound or not, can be treated according to methods which comprise:

preparing one or more solutions of metal compounds to be carried on a medium;
impregnating the zeolite with the above solutions;
drying the zeolite thus impregnated;
calcining the impregnated and dried zeolite, at temperatures ranging from 400 to 650° C.;

optionally repeating the previous steps once or several times according to necessity.

Examples of metal compounds used are; molybdenum(II) acetate, ammonium(VI) molybdate, diammonium(III) dimolybdate, ammonium (VI) heptamolybdate, ammonium(VI) phosphomolybdate, and analogous sodium and potassium salts, molybdenum(III) bromide, molybdenum(III)-(V) chloride, molybdenum(VI) fluoride, molybdenum(VI) oxychloride, molybdenum(IV)-(VI) sulfide, molybdic acid and the corresponding acid ammonium, sodium and potassium salts, and molybdenum(II-VI) oxides; cobalt(II) acetate, cobalt(II) acetylacetonate, cobalt(III) acetylacetonate, cobalt(II) benzoylacetonate, cobalt(II) 2-ethylhexanoate, cobalt(II) chloride, cobalt(II) bromide, cobalt(II) iodide, cobalt(II)-(III) fluoride, cobalt(II) carbonate, cobalt(II) nitrate, cobalt(II) sulfate; nickel(II) acetate, nickel(II) acetylacetonate, nickel (II) bromide, nickel(II) carbonate, nickel(II) nitrate, nickel (II) chloride, nickel(II) iodide, nickel(II) molybdate, nickel (II) sulfate; zinc(II) acetate, zinc(II) acetylacetonate, zinc(II) chloride, zinc(II) bromide, zinc(II) citrate, zinc(II) tartrate, zinc(II) fluoride, zinc(II) iodide, zinc(II) molybdate, zinc(II) nitrate, zinc(II) sulfate, zinc(II) sulfide; palladium(II) acetate, palladium (II) acetylacetonate, palladium(II) bromide, palladium(II) chloride, palladium(II) iodide, palladium(II) nitrate, palladium(II) sulfate, palladium(II) sulfide, palladium (II) trifluoro acetate.

At the end of the impregnation, the total content of metal, single or in pairs, in the catalyst ranges from 0.1 to 10% by weight, preferably from 0.5 to 8% by weight.

At the end of the preparation of the catalyst, this is charged into a fixed bed reactor fed in continuous with the hydrocarbon charge and hydrogen. In this respect, not only is the control of the experimental parameters so far described of absolute importance, but also the selection of the flow-rate of the reagents, in order to obtain a hydrodealkylation selectivity of the $C_8$-$C_{13}$ aromatic hydrocarbons optionally mixed with $C_4$-$C_9$ aliphatic and cycloaliphatic hydrocarbons. The feeding flow-rates of the hydrocarbon and hydrogen mixture must be such as to guarantee an LHSV (Liquid Hourly Space Velocity), calculated with respect to the hydrocarbon stream, ranging from 3 to 5 $h^{-1}$ and, more preferably, from 3.5 to 4.5 $h^{-1}$. For this purpose, the molar ratio between the hydrogen and charge fed must remain within a range of 3 to 6 mole/mole, more preferably from 3.8 to 5.2 mole/mole.

An experimental apparatus is used, which comprises a fixed bed reactor made of stainless steel with an internal diameter of 20 mm and a total height of 84.5 cm, an electric heating device which surround the reactor, a cooling device, a gas-liquid separator and a high pressure liquid pump.

The isothermal section of the reactor, maintained at a constant temperature by means of automatic control, is charged with the catalyst. The remaining volume of the reactor is filled with an inert solid in granules, for example corundum, to guarantee an optimal distribution and mixing of the gaseous stream of reagents before the catalytic bed and of the heat supplied to the reaction.

A preheater situated before the reactor which operates at a temperature ranging from 200 to 400° C., preferably from 250 to 320° C., also contributes to ensuring an optimum contact of the reagents (charge and hydrogen) in gaseous phase with the catalyst. This system favours the establishment of isothermal conditions in very rapid times, not limited to the fixed bed alone but along the whole reactor enabling an easier and more accurate control of the operation temperature of the catalyst. The liquid and gaseous effluents produced by the reaction are separated and analyzed by gas chromatography at intervals.

The following examples provide a further illustration of the process according to the present invention but should in no way be considered as limiting its scope which is indicated in the enclosed claims.

REFERENCE EXAMPLE FOR THE PREPARATION OF THE CATALYSTS

Catalyst A (Comparative)

Catalyst A is prepared, obtained by mixing a ZSM-5 zeolite and an alumina as binder, the two phases being in a weight ratio of 60/40, and extruding the mixture.

The extruded product is calcined in air at 550° C. for 5 hours and its BET surface area is 290 $m^2/g$.

Once this has reached room temperature, it is crushed and sieved to produce a powder having a dimension ranging from 20 to 40 mesh (from 0.84 mm to 0.42 mm), so that 12.4 g of catalyst powder occupy an equivalent volume of 20 ml.

Catalyst B

Catalyst B is obtained by impregnating catalyst A (50 g) with an aqueous solution (60 ml) containing 1.88 g of ammonium molybdate [$(NH_4)_6MO_7O_{24} \cdot 4H_2O$] at about 25° C. for 16 hours and subsequently put under a nitrogen stream for 12 hours, dried in an oven at 120° C. for 4 hours under vacuum and calcined in air at 550° C. for 5 hours. The calculated molybdenum content in the catalyst is 2.0% by weight, with respect to the value of 2.1% determined by means of ICP-MS analysis.

Catalyst C

Catalyst C is obtained by impregnating Catalyst A (14 g) with an aqueous solution (17 ml) containing 0.78 g of ammonium molybdate [$(NH_4)_6MO_7O_{24}.4H_2O$], and subsequently following the procedure used for preparing Catalyst B. The calculated molybdenum content is 3.0% weight, in accordance with the value of 3.05% by weight obtained via ICP-MS.

Catalyst D

Catalyst D is obtained by impregnating Catalyst A (50 g) with an aqueous solution (60 ml) containing 3.76 g of ammonium molybdate [$(NH_4)_6MO_7O_{24}.4H_2O$], and subsequently following the procedure used for the preparation of Catalyst A. The calculated molybdenum content is 3.9% weight, in accordance with the value of 4.1% by weight obtained via ICP-MS.

Catalyst E

Catalyst E is obtained by impregnating Catalyst A (50 g) in two steps: a first impregnation with an aqueous solution (60 ml) containing 1.88 g of ammonium molybdate [$(NH_4)_6MO_7O_{24}.4H_2O$], followed by a second impregnation with an aqueous solution (50 ml) containing 2.77 g of zinc acetate dihydrate [$Zn(OCOCH_3)_2.2H_2O$]. The impregnation procedure with the first metal is carried out as described for catalyst B, but without calcinations, followed by impregnation with the second metal using the same operating procedure, and final calcination in air at 550° C. for 5 hours.

The calculated molybdenum and zinc content in the catalyst is 2.0% by weight and 1.69 by weight, respectively, compared with the values of 2.0% by weight and 1.7% by weight determined by ICP-MS.

Catalyst F

Catalyst F is obtained by impregnating Catalyst A (20 g) in two steps: a first impregnation with an aqueous solution (24 ml) containing 1.15 g of ammonium molybdate [$(NH_4)_6MO_7O_{24}.4H_2O$], followed by a second impregnation with an aqueous solution (23 ml) containing 0.5 g of cobalt nitrate hexahydrate [$Co(NO_3)_2.6H_2O$]. The impregnation procedure with the two metals is carried out as described for catalyst E.

The calculated molybdenum and cobalt content in the catalyst is 3.0% by weight and 0.5% by weight, respectively, compared with the values of 3.0% by weight and 0.5% by weight determined by ICP-MS.

Catalyst G

Catalyst G is obtained by impregnating Catalyst A (50 g) with an aqueous solution (50.5 ml) containing 1.85 g of nickel nitrate [$Ni(NO_3)_2.6H_2O$], following the procedure used for preparing Catalyst B.

The calculated nickel content is 0.749 weight with respect to the value of 0.77% by weight obtained via ICP-MS.

Catalyst H

Catalyst H is obtained by impregnating Catalyst A (50 g) with an aqueous solution (60 ml) containing 4.0 g of nickel nitrate [$Ni(NO_3)_2.6H_2O$], following the procedure used for preparing Catalyst B.

The calculated nickel content is 1.6% weight with respect to the value of 1.7% by weight obtained via ICP-MS.

Catalyst I

Catalyst I is obtained by impregnating Catalyst A (14 g) with an aqueous solution of 0.6 g of palladium acetate [$Pd(OCOCH_3)_2$] in 20 ml of acetone, following the procedure used for preparing Catalyst B.

The calculated palladium content is 2.0% weight compared with the value of 2.1% by weight obtained via ICP-MS.

Examples 1-4

Comparative

The reactor is charged with 20 cm$^3$ (12.4 g) of catalyst A, whereas the remaining volume is filled with corundum in granules to guarantee an optimum distribution and mixing of the gaseous stream of reagents and of the heat supplied to the reaction.

Two different charges, whose composition is indicated in Table 1 below, suitably mixed with hydrogen and preheated to 280° C., are fed, alternately, to the reactor. In both charges, the aliphatic part is carried by the $C_4$-$C_9$ products and by the saturated $C_5$ indane ring.

TABLE 1

Composition of the feeding charge

| | Charge 1 weight % | Charge 2 weight % |
|---|---|---|
| Ethylbenzene | 43 | 34 |
| o,m,p-xylene | 20 | 32 |
| indane | 12 | 9 |
| cumene | 1 | 1 |
| n-propylbenzene | 3 | 3 |
| 2-,3-,4-ethyltoluene | 16 | 16 |
| Σ ($C_4$-$C_9$ Aliphat. + $C_{9+}$ Arom.) | 5 | 5 |
| Total | 100 | 100 |

The reaction is carried out at a pressure of 3 MPa with a reagent charge flow rate so as to have an LHSV of 3.9-4.1 h$^{-1}$, and a molar ratio $H_2$/charge of 4.2-4.4. The results are shown in Table 2 below.

TABLE 2

| | Ex. 1 | Ex. 2 | Ex. 3 | Ex. 4 |
|---|---|---|---|---|
| Catalyst | A | A | A | A |
| Metal | — | — | — | — |
| Reaction temperature | 450° C. | 510° C. | 510° C. | 550° C. |
| Charge | Charge 1 | Charge 1 | Charge 2 | Charge 2 |
| Charge conversion (%) | 80.0 | 80.2 | 78.6 | 81.3 |

TABLE 2-continued

|  | Ex. 1 | Ex. 2 | Ex. 3 | Ex. 4 |
|---|---|---|---|---|
| Liquid effluent composition | weight % | weight % | weight % | weight % |
| Methane | 3.2 | 6.9 | 10.3 | 13.8 |
| Σ $C_2$ | 7.0 | 10.8 | 11.2 | 11.4 |
| Σ $C_3$ | 7.9 | 3.0 | 3.1 | 1.3 |
| Σ $C_4$-$C_5$ | 0.1 | 0.1 | — | — |
| Ethylbenzene | 2.6 | 1.5 | 0.9 | 0.8 |
| o,m,p-xylene | 15.1 | 14.8 | 15.9 | 14.5 |
| indane | — | — | — | — |
| cumene | — | — | — | — |
| Σ $C_9$-$C_{9+}$ aromatic | 6.9 | 5.6 | 5.5 | 5.0 |
| Benzene | 27.4 | 26.6 | 24.0 | 26.3 |
| Toluene | 29.6 | 31.1 | 28.4 | 26.9 |
| Total | 100.0 | 100.0 | 100.0 | 100.0 |
| Σ (Bz + Tol) | 57.0 | 57.7 | 52.4 | 53.3 |
| Selectivity to (Bz + Tol) (w %) | 71.3 | 71.9 | 66.7 | 65.6 |
| R (Bz + Tol) | 0.93 | 0.86 | 0.76 | 0.98 |

Examples 5-20

The same procedure is used as in the previous examples 1-4, with the substantial difference that catalyst A is substituted by catalysts B-I described above. The results are indicated in the enclosed tables 3, 4 and 5.

TABLE 3

|  | Ex. 1 | Ex. 5 | Ex. 6 | Ex. 7 | Ex. 8 | Ex. 9 |
|---|---|---|---|---|---|---|
| Catalyst | A | B | D | G | H | I |
| Metals | — | Mo 2% w | Mo 4% w | Ni 0.8% w | Ni 1.7% w | Pd 2% w |
| Reaction temperature | 450° C. | 450° C. | 450° C. | 450° C. | 450° C. | 450° C. |
| Charge | Charge 1 | Charge 1 | Charge 1 | Charge 1 | Charge 1 | Charge 2 |
| Charge conversion (%) | 80.0 | 81.8 | 80.7 | 81.2 | 83.2 | 81.4 |
| Liquid effluent composition | weight % | weight % | weight % | weight % | weight % | weight % |
| Methane | 3.2 | 0.6 | 0.4 | 1.7 | 1.7 | 0.4 |
| Σ $C_2$ | 7.0 | 19.0 | 18.0 | 11.4 | 14.5 | 18.0 |
| Σ $C_3$ | 7.9 | 2.7 | 2.1 | 5.9 | 5.5 | 3.1 |
| Σ $C_4$ - $C_5$ | 0.1 | 0.1 | — | 0.1 | 0.1 | 0.1 |
| Ethylbenzene | 2.6 | 0.7 | 0.5 | 2.3 | 1.1 | 0.2 |
| o, m, p-xylene | 15.1 | 15.9 | 14.6 | 14.3 | 13.7 | 15.6 |
| indane | — | — | — | — | — | — |
| cumene | — | — | — | — | — | — |
| Σ $C_9$ - $C_{9+}$ aromatic | 6.9 | 3.2 | 4.3 | 5.7 | 4.4 | 3.8 |
| Benzene | 27.4 | 37.1 | 37.5 | 30.6 | 31.5 | 29.5 |
| Toluene | 29.6 | 20.7 | 22.6 | 28.0 | 27.5 | 29.3 |
| Total | 100.0 | 100.0 | 100.0 | 100.0 | 100.0 | 100.0 |
| Σ (Bz + Tol) | 57.0 | 57.8 | 60.1 | 58.6 | 59.0 | 58.8 |
| Selectivity to (Bz + Tol) (w %) | 71.3 | 70.7 | 74.5 | 72.2 | 70.9 | 72.2 |
| R (Bz + Tol) | 0.93 | 1.79 | 1.66 | 1.09 | 1.15 | 1.01 |

TABLE 4

|  | Ex. 10 | Ex. 11 | Ex. 12 | Ex. 13 | Ex. 14 | Ex. 15 | Ex. 16 | Ex. 17 | Ex. 18 |
|---|---|---|---|---|---|---|---|---|---|
| Catalyst | B | B | B | C | C | G | H | I | I |
| Metals | Mo 2% w | Mo 2% w | Mo 2% w | Mo 3% w | Mo 3% w | Ni 0.8% w | Ni 1.7% w | Pd 2% w | Pd 2% w |
| Reaction temperature | 510° C. | 510° C. | 550° C. | 510° C. | 550° C. | 510° C. | 510° C. | 510° C. | 525° C. |
| Charge | Charge 1 | Charge 2 | Charge 2 | Charge 2 | Charge 2 | Charge 1 | Charge 1 | Charge 2 | Charge 2 |
| Charge conversion (%) | 85.8 | 84.5 | 88.7 | 86.0 | 86.5 | 83.6 | 85.2 | 86.2 | 87.0 |
| Liquid effluent composition | weight % | weight % | weight % | weight % | weight % | weight % | weight % | weight % | weight % |
| Methane | 1.3 | 3.2 | 7.0 | 1.0 | 3.5 | 3.5 | 5.8 | 2.8 | 2.9 |
| Σ $C_2$ | 17.3 | 20.6 | 19.2 | 18.1 | 17.7 | 12.3 | 14.1 | 16.5 | 16.8 |
| Σ $C_3$ | 2.0 | 3.8 | 2.2 | 1.4 | 1.4 | 5.0 | 2.6 | 1.9 | 0.9 |
| Σ $C_4$ - $C_5$ | 0.1 | 0.1 | 0.1 | — | — | 0.1 | — | — | — |
| Ethylbenzene | 0.3 | 0.2 | 0.1 | 0.1 | 0.5 | 0.2 | 0.1 | 0.1 | 0.1 |
| o, m, p-xylene | 10.4 | 13.1 | 10.0 | 9.9 | 12.4 | 13.7 | 12.4 | 11.4 | 10.9 |
| indane | — | — | — | — | — | — | — | — | — |
| cumene | — | — | — | — | — | — | — | — | — |
| Σ $C_9$ - $C_{9+}$ aromatic | 3.9 | 3.0 | 1.9 | 4.0 | 1.8 | 4.6 | 3.0 | 3.1 | 4.0 |
| Benzene | 35.4 | 27.2 | 29.6 | 36.0 | 29.9 | 32.8 | 30.3 | 32.9 | 34.4 |
| Toluene | 29.3 | 28.8 | 29.9 | 29.5 | 32.8 | 27.4 | 30.8 | 31.3 | 30.0 |
| Total | 100.0 | 100.0 | 100.0 | 100.0 | 100.0 | 100.0 | 100.0 | 100.0 | 100.0 |
| Σ (Bz + Tol) | 64.7 | 56.0 | 59.5 | 65.5 | 62.7 | 60.2 | 61.1 | 64.2 | 64.4 |
| Selectivity (Bz + Tol) (w %) | 75.4 | 66.3 | 67.1 | 76.2 | 72.5 | 72.0 | 71.7 | 74.5 | 74.0 |
| R (Bz + Tol) | 1.21 | 0.94 | 0.99 | 1.22 | 0.91 | 1.20 | 0.98 | 1.05 | 1.15 |

TABLE 5

|  | Ex. 19 | Ex. 20 |
|---|---|---|
| Catalyst | E | F |
| Metals | Zn 1.7% w + Mo 2% w | Co 0.5% w + Mo 3% w |
| Reaction temperature | 510° C. | 450° C. |
| Charge | Charge 2 | Charge 2 |
| Charge conversion (%) | 84.3 | 80.3 |
| Liquid effluent composition | weight % | weight % |
| Methane | 3.8 | 1.0 |
| $\Sigma\ C_2$ | 16.5 | 19.7 |
| $\Sigma\ C_3$ | 5.7 | 2.8 |
| $\Sigma\ C_4\text{-}C_5$ | 0.1 | 0.1 |
| Ethylbenzene | 0.8 | 0.3 |
| o,m,p-xylene | 13.1 | 17.0 |
| indane | — | — |
| cumene | — | — |
| $\Sigma\ C_9\text{-}C_{9+}$ aromatic | 3.3 | 3.6 |
| Benzene | 29.6 | 32.6 |
| Toluene | 27.1 | 22.9 |
| Total | 100.0 | 100.0 |
| $\Sigma$ (Bz + Tol) | 56.7 | 55.5 |
| Selectivity to (Bz + Tol) (w %) | 67.3 | 69.1 |
| R (Bz + Tol) | 1.09 | 1.42 |

The hydrodealkylation reaction carried out at a temperature of 450° C. with Charge 1 (see Table 3) shows how the presence of one of the metals and ZSM-5, according to the invention, distinctly favours the selective dealkylation of the aromatics, by inhibiting the by-production of methane to favour the net increase in ethane, with respect to the reaction carried out with the catalyst as such (Example 1). Furthermore, not only is the production of benzene and toluene increased, but their weight ratio (benzene/toluene) becomes unexpectedly and distinctly favourable towards benzene (Examples 5-8). In the case of the reaction carried out on Charge 2 (Example 9) in addition to the positive results already indicated for Charge 1, it is observed that even with a greater quantity of xylenes (about 1.5 times by weight with respect to Charge 1), their concentration in the effluent does not increase, maintaining the typical value of that relating to the effluent deriving from the reaction carried out on Charge 1.

This further evidence indicates the capacity of the process, object of the invention, of guaranteeing, also in the case of a "heavier" charge, by an increase in the content of xylenes, a selective dealkylation without concomitant isomerization, transalkylation, disproportioning and condensation reactions.

At temperatures higher than 450° C. (Table 4) and always in the presence of the catalyst impregnated with metal, further significant increases in the conversion of the charges (1 and 2) and selectivity to benzene plus toluene, are contemporaneously obtained, with a ratio between the benzene and toluene produced which is still favourable towards benzene. The increased selectivity observed with respect to the products obtained in the liquid phase, is also observed in the gaseous phase, where an increase in the production of ethane is registered, whereas the increase in the concentration of methane is directly connected to the further reduction in the content of xylenes and $C_9\text{-}C_{9+}$ aromatics which are selectively dealkylated (Examples 10-18).

This result is particularly important as the amount of xylenes and higher aromatics converted per single passage by the process object of the invention is such as to sustain the recycling of what remains in the effluent.

The hydrodealkylation reaction carried out with a catalyst impregnated with pairs of metals, at both 450° C. and 510° C., (Examples 19-20, Table 5) further improves, with respect to the single metal, the benzene/toluene ratio, i.e. it makes the reaction towards benzene, total dealkylation product, even more selective.

Examples 2 bis, 5 bis, 10 bis

Table 6 indicates the examples relating to hydrodealkylation reactions carried out in the previous examples with the substantial difference that sulfur is added to Charge 1 in the form of dimethyl disulfide (DMDS).

TABLE 6

|  | Ex. 2 | Ex. 2 bis | Ex. 5 | Ex. 5 bis | Ex. 10 | Ex. 10 bis |
|---|---|---|---|---|---|---|
| Catalyst | A | A | B | B | B | B |
| Metals | — | — | Mo 2% w | Mo 2% w | Mo 2% w | Mo 2% w |
| Reaction temperature | 510° C. | 510° C. | 450° C. | 450° C. | 510° C. | 510° C. |
| Charge | Charge 1 | Charge 1 | Charge 1 | Charge 1 | Charge 1 | Charge 1 |
| Presence of DMDS (ppm/w)* | — | 200 | — | 200 | — | 200 |
| Charge conversion (%) | 80.2 | 82.8 | 81.8 | 82.0 | 85.8 | 85.1 |
| Benzene | 26.6 | 24.7 | 37.1 | 36.0 | 35.4 | 33.7 |
| Toluene | 31.1 | 29.8 | 20.7 | 21.4 | 29.3 | 30.3 |
| $\Sigma$ (Bz + Tol) | 57.7 | 54.5 | 57.8 | 57.4 | 64.7 | 64.0 |
| Selectivity to (Bz + Tol) (w %) | 71.9 | 65.8 | 70.7 | 70.0 | 75.4 | 75.2 |
| R (Bz + Tol) | 0.86 | 0.83 | 1.79 | 1.68 | 1.21 | 1.11 |

*equal to 136 ppm/w as sulfur equivalent

Under the process conditions, object of the invention, the charge is quantitatively hydro-desulfurated as the corresponding $H_2S$ remains lower than 0.5 ppm/w in the liquid effluent.

The examples of Table 6 demonstrate that the hydrodealkylation reaction proceeds without any alternation in the catalytic activity when the catalyst is impregnated with the metal. In particular, it is evident that already at 450° C., the results obtained of yield to benzene plus toluene and the benzene/toluene ratio are distinctly higher than those obtained at 510° C. with the non-treated catalyst, whereas the conversions of the charge at the two temperatures are identical.

The invention claimed is:

1. A process for the catalytic hydrodealkylation alone of hydrocarbons comprising $C_8$-$C_{13}$ alkylaromatic compounds, optionally mixed with $C_4$-$C_9$ aliphatic and cycloaliphatic products, which comprises treating said hydrocarbon compositions, in continuous and in the presence of hydrogen, with a ZSM-5 zeolite catalyst having an Si/Al molar ratio ranging from 5 to 35, modified with at least one metal selected from the group consisting of those belonging to groups IIB, VIB, VIII, at a temperature ranging from 400 to 650° C., a pressure ranging from 2 to 4 MPa and an $H_2$/charge molar ratio ranging from 3 to 6.

2. The process according to claim 1, wherein the hydrodealkylation reaction takes place at temperatures ranging from 450 to 580° C., pressures ranging from 2.8 to 3.6 MPa, $H_2$/charge molar ratios ranging from 3.8 to 5.2, and with flow-rates of the reagents which are to guarantee an LHSV (Liquid Hourly Space Velocity), calculated, with respect to the hydrocarbon stream, ranging from 3 to 5 $h^{-1}$.

3. The process according to claims 1, wherein the hydrocarbon charge subjected to hydrodealkylation comprises $C_8$-$C_{13}$ alkylaromatic compounds selected from the group consisting of ethylbenzene, xylenes, propylbenzenes, ethyltoluenes, trimethylbenzenes, diethylbenzenes, ethylxylenes, tetramethylbenzenes, propyltoluenes, ethyltrimethylbenzenes, triethylbenzenes, and dipropyltoluenes.

4. The process according to claim 3, wherein the $C_8$-$C_{13}$ alkylaromatic hydrocarbon charge comes from reforming units or from units effecting pyrolytic processes, or from steam cracking.

5. The process according to claim 1, wherein the hydrocarbon charge subjected to hydrodealkylation comprises $C_8$-$C_{13}$ alkylaromatic compounds, optionally mixed with $C_4$-$C_9$ aliphatic and cycloaliphatic products and organic compounds containing hetero-atoms.

6. The process according to claim 1, wherein the ZSM-5 zeolite catalyst is in bound form, with binders selected from the group consisting of aluminas; silica; alumino-silicates; titanium and zirconium oxides; and their mixtures with zeolite/binder weight ratios ranging from 100/1 to 1/10.

7. The process according to claim 6, wherein the ZSM-5 catalyst/binder is modified with at least one metal selected from the group consisting of those belonging to groups IIB, VIB, and VIII.

8. The process according to claim 7, wherein the metal is selected from the group consisting of molybdenum, zinc, nickel, cobalt, palladium, and their mixtures.

9. The process according to claim 8, wherein the metal is molybdenum.

10. The process according to claim 1, wherein the ZSM-5 zeolite is characterized by an Si/Al molar ratio ranging from 15 to 30.

11. The process according to claim 1, wherein the dispersion of metals on the catalyst can be carried out according to techniques selected from impregnation, ion exchange, vapor deposition or surface adsorption.

12. The process according to claim 1, wherein the ZSM-5 zeolite as such or in bound form is impregnated with metals of groups IIB, VIB and VIII according to methods which comprise:
   preparing one or more solutions of metal compounds to be carried on a medium;
   impregnating the zeolite with the above solutions;
   drying the zeolite thus impregnated;
   calcining the impregnated and dried zeolite, at temperatures ranging from 400 to 650° C.; and
   optionally repeating the previous steps once or several times.

13. The process according to claim 12, wherein the dispersion of metals on the catalyst takes place by impregnation with an aqueous or aqueous-organic solution, with the organic solvent selected from the group consisting of alcohols, ketones, nitriles, and their mixtures, containing at least one hydro- or organo-soluble compound of the metal in such concentrations that the total final content of the metal in the catalyst ranges from 0.1 to 10% by weight.

14. The process according to claim 1, wherein the total content of the metal in the catalyst ranges from 0.5 to 8% by weight.

15. The process according to claim 2, wherein the LHSV ranges from 3.5 to 4.5 $h^{-1}$.

16. The process according to claim 6, wherein the aluminas are selected from the group consisting of pseudo-bohemite and γ-alumina.

17. The process according to claim 6, wherein the clays are selected from the group consisting of kaolinite, smectites, montmorillonites.

* * * * *